(12) United States Patent
Bammer et al.

(10) Patent No.: US 9,395,716 B2
(45) Date of Patent: Jul. 19, 2016

(54) DRUG DISPENSING DEVICE

(71) Applicants: SEIBERSDORF LABOR GMBH, Seibersdorf (AT); AIT AUSTRIAN INSTITUTE OF TECHNOLOGY GMBH, Vienna (AT)

(72) Inventors: Manfred Bammer, Vienna (AT); Gernot Schmid, Bromberg (AT); Otmar Putz, Bromberg (AT)

(73) Assignees: Seibersdorf Labor GmbH, Seibersdorf (AT); AIT Austrian Institute of Technology GmbH, Vienna (AT)

( * ) Notice: Subject to any disclaimer, the term of this patent is extended or adjusted under 35 U.S.C. 154(b) by 0 days.

(21) Appl. No.: 14/433,704

(22) PCT Filed: Sep. 17, 2013

(86) PCT No.: PCT/AT2013/050187
§ 371 (c)(1),
(2) Date: Apr. 6, 2015

(87) PCT Pub. No.: WO2014/052997
PCT Pub. Date: Apr. 10, 2014

(65) Prior Publication Data
US 2015/0268656 A1    Sep. 24, 2015

(30) Foreign Application Priority Data
Oct. 5, 2012   (AT) .................. A50428/2012

(51) Int. Cl.
*G01F 23/26*   (2006.01)
*G05B 19/18*   (2006.01)
(Continued)

(52) U.S. Cl.
CPC .......... *G05B 19/188* (2013.01); *A61M 5/1684* (2013.01); *A61M 5/24* (2013.01); *G01F 23/266* (2013.01); *G01F 23/268* (2013.01);
(Continued)

(58) Field of Classification Search
CPC ............... B60L 15/2009; B60W 30/18063; Y02T 10/645; Y02T 10/7275; A61M 2205/3317; A61M 2205/3379; A61M 2205/3389; A61M 5/14566; A61M 5/1782; A61M 5/28; A61M 5/31566; A61M 5/31573; G01F 11/027
See application file for complete search history.

(56) References Cited

U.S. PATENT DOCUMENTS 4,237,878 A  * 12/1980  Kobayashi .......... A61M 5/1684
                                                128/DIG. 13
4,749,988 A  *  6/1988  Berman ................ G01F 23/268
                                                340/618

(Continued)

FOREIGN PATENT DOCUMENTS

WO    2007107558 A2    9/2007

*Primary Examiner* — John Fitzgerald
*Assistant Examiner* — Gedeon M Kidanu
(74) *Attorney, Agent, or Firm* — Laurence A. Greenberg; Werner H. Stemer; Ralph E. Locher (57) ABSTRACT

A dispensing device for dispensing liquids, particularly liquid medications to people, contains a container which is filled with a liquid and which has an opening at one end for dispensing same. The dispensing device further has at least one pair of capacitive measuring electrodes which are arranged in an outer region of the container, particularly on the wall, opposite one another, for determining the permittivity of the respective medium in the intermediate region between the measuring electrodes. A shield is arranged around the container and surrounds the measurement electrodes in a sheath-like manner.

17 Claims, 11 Drawing Sheets (51) Int. Cl.
 *A61M 5/24* (2006.01)
 *A61M 5/168* (2006.01)
(52) U.S. Cl.
 CPC .............. *A61M2205/3317* (2013.01); *A61M 2205/3389* (2013.01); *A61M 2205/3561* (2013.01); *G05B 2219/45235* (2013.01)

(56) References Cited

U.S. PATENT DOCUMENTS

| | | | | |
|---|---|---|---|---|
| 6,110,148 A | * | 8/2000 | Brown | A61M 5/1782 222/23 |
| 6,186,176 B1 | * | 2/2001 | Gelbmann | G05D 7/03 137/251.1 |
| 6,490,920 B1 | * | 12/2002 | Netzer | G01C 9/06 324/687 |
| 2003/0117206 A1 | * | 6/2003 | Ohnakado | H01L 27/0251 327/310 |
| 2004/0110277 A1 | * | 6/2004 | Maeda | G01N 33/5438 435/287.2 |
| 2006/0201234 A1 | * | 9/2006 | Abe | G01N 27/22 73/53.01 |
| 2007/0157718 A1 | * | 7/2007 | Woodard | G01F 23/268 73/149 |
| 2009/0069756 A1 | * | 3/2009 | Larsen | A61M 5/14566 604/246 |
| 2009/0120159 A1 | * | 5/2009 | Barlesi | G01F 23/266 73/1.73 |
| 2013/0042678 A1 | * | 2/2013 | Studer | A61M 5/148 73/299 |
| 2013/0136672 A1 | * | 5/2013 | Blumentritt | B01L 3/0275 422/524 |

* cited by examiner

DRUG DISPENSING DEVICE

BACKGROUND OF THE INVENTION

Field of the Invention

The invention concerns a device for dispensing fluids, in particular liquid drugs to persons according to the generic terms of the main device claim. The invention further concerns a method for determining and validating the fill level in a container according to the generic terms of the main method claim.

The invention may be used, in particular, in health care, e.g., in medical technology, pharmaceuticals, and biotechnology, medicine and nursing, studies, to monitor the dispensing of drugs to patients.

Various devices for dispensing fluids are known from the prior art in which the liquid dispensed is determined on a capacitive basis. This invention seeks to effectively detect malfunctions in capacitive fill level detection and to allow for the invalidation of capacitive fill level readings. The invention further seeks to provide the best, most reliable results possible.

BRIEF SUMMARY OF THE INVENTION

The invention meets this objective in the form of a dispensing device of the aforementioned type having the distinguishing characteristic of the main device claim.

This invention further meets this objective by means of a method of the aforementioned type with the characteristic in the characterising portion of the main method claim.

According to the invention, the following is provided in a device for dispensing fluids, in particular liquid drugs, to persons:
  a container filled with the liquid having an opening for dispensing the liquid on one end, as well as
  at least one pair of capacitive measurement electrodes arranged on the outside, in particular on the wall, of the container opposite one another to determine the permittivity of the respective medium in the intermediate space between the measurement electrodes, comprising a cover surrounding the measurement electrodes and arranged around the container.

Failures, which are caused by touching the container during the measurement process due to capacitive effects, are effectively avoided with the invention.

In particular, the measure according to the invention can prevent contact between the measurement electrodes and a person's hand or a falsification of the field in the area of the measurement electrodes by a person's hand, which may cause changes in the fill level reading.

Advantageously, the cover may be formed as a film coated with tracks consisting of electrically conductive material. In a preferred embodiment, this film is arranged or wrapped around the container. Such a cover prevents the falsification of measurements in a particularly advantageous manner.

Advantageously, the area between the liquid and the measurement electrodes is not covered by the cover.

In order to prevent deterioration of the readings due to the effects of the cover, it may be provided for the cover to be spaced apart radially from the measurement electrodes.

In order to obtain better protection and simultaneously allow for the attachment of a semiconductor chip and an antenna in the area of the cover or on the film, it may be provided for the cover to be formed as a film, in particular wrapped around the container, coated with conductors in the form of tracks, whereby, preferably, a capacity measurement arrangement, a processing unit, and a communication controller, in particular in the form of a semiconductor chip, as well as an antenna are attached to the film.

In order to avoid a change in the electromagnetic field generated by an external data communications device that may impair wireless communication with the antenna whilst obtaining good electrical insulation of the measurement electrodes, it may be provided for the conductors to be free of loops and/or free of closed conductor loops.

A particularly advantageous configuration of a cover that simultaneously can be used for contact detection and also allows for wireless communication with an antenna attached to the cover, provides for two separate conductors to be formed on the film, whereby the first and second conductor are formed as mutually engaging comb conductors and the third conductor is meander-shaped and arranged between the two comb conductors.

A preferred measure for determining the fill level of the liquid inside the container provides for the two measurement electrodes arranged opposite one another to be connected to a capacity measurement device.

For a simple determination of the fill level, it may be provided for the capacity reading obtained by the capacity measurement device to be provided to a processing unit that determines the fill level of the liquid in the container by means of a specified and stored calibration function and makes it available at its output.

Particularly effective coverage with good protective effect can be obtained by connecting one of the three conductors, in particular the second conductor that is formed as a comb conductor, with the reference connection of the capacity measurement device.

In order to advantageously determine contact or falsifications of the capacity measurement, a contact sensor, in particular a capacitive contact sensor, arranged outside of, or in the area of, the cover may be provided.

An easily produced variant provides for the contact sensor to comprise the first comb connector and the meander-shaped conductor of the cover as sensor electrodes.

To detect contact, it may be provided for the sensor electrodes of the contact sensor to be connected to another capacity measurement device, and preferably for the additional capacity reading determined by the other capacity measurement device to be provided to the processing unit, and for the processing unit to prevent the forwarding of or mark as invalid the fill level determined by it in the event that the additional capacity reading exceeds a specified threshold level.

An advantageous container for receiving fluids that can be simply emptied, and the fill level of which can be simply determined, provides for the container to have an internal volume that, apart from the area of the opening, has a constant inner cross section, whereby a plunger sealing the container and the liquid contained in it is provided, the external cross section of which corresponds to the cross-section of the internal volume of the container, and which is arranged movably inside the container, such that movement of the plunger towards the opening causes the liquid to be dispensed from the container through the opening.

For more precise determination of the fill level, it may be provided for numerous pairs of additional measurement electrodes to be arranged on the container, whereby, in particular, for each pair of additional measurement electrodes one additional capacity measurement device associated with each respective pair of additional measurement electrodes that provides the capacity reading obtained to the processing unit.

An advantageous electrode configuration allowing for precise determination of the fill level provides for the respectively paired measurement electrodes to be opposite—in particular diametrically opposite—one another in the circumferential direction, and in particular to be at the same height in the direction of movement of the plunger.

To improve the detection accuracy, it may additionally be provided for respectively adjacent pairs of measurement electrodes to be spaced apart in the direction of movement of the plunger, and/or for the width of the measurement electrodes in the direction of movement of the plunger to correspond to the width of the plunger in its direction of movement.

Preferred embodiments of the measurement electrodes with a simple structure provide:
for the measurement electrodes to be arranged extensively on the outer surface of the container, and in particular to be in the form of a rectangle, triangle, trapezoid, or parallelogram, and/or for two each of the paired measurement electrodes to be formed by two mutually engaged comb connectors arranged on the outside, in particular on the outer wall, of the container.

In order to allow for easy replacement of the container, it may be provided for a support to be arranged outside the container between the container and the cover, on which the measurement electrodes are arranged, whereby the support preferably abuts the container and/or for the measurement electrodes to be arranged on the wall of the support abutting the container.

Advantageously, the fill level determined may be transmitted to an external communications device. It may be provided for a communications controller with a downstream antenna to be connected to the processing unit. For a space-saving configuration, it may advantageously be provided for the antenna to be arranged outside the cover or immediately on the cover, but not connected to it in an electrically conductive manner.

Additionally, the invention concerns a method for determining and validating the fill level in a container that is arranged, in particular, in a dispensing device according to the invention, whereby at least one pair of measurement electrodes arranged opposite one another on the outside of the container, in particular having an outer cover, is provided for capacity measurement whereby the capacity between the two measurement electrodes is determined and a fill level reading is obtained based on the capacity determined according to a specified calibration function.

According to the invention, in such a method, it is provided:
for another capacity to be determined with conductors arranged outside the measurement electrodes in the area of the cover, in particular on the cover,
for the other capacity to be compared with a threshold value, and
for the fill level reading only to be considered valid if the other capacity is below the threshold level.

Such a method allows for simple verification of whether the fill level determined was falsified by a person touching the measurement electrodes or cover in the area of the measurement electrodes, or has come near enough to the measurement electrodes to cause a falsification.

For accurate determination of the fill level, it may be provided for the fill level and/or information concerning the validity of the fill level to be transmitted by encoded electromagnetic data transmission, in particular by load modulation, to an external data communications device.

For the same purpose, it may be provided for the capacities of multiple, in particular three, pairs of measurement electrodes arranged opposite one another on the outside of the container, each to be determined and for the fill level to be determined based on the capacities.

Particular accurate detection is possible by
a) providing respective reference vectors comprising the capacities between the individual pairs of measurement electrodes as components for a number of fill levels, and
b) associating the respective fill level with each of these vectors,
c) determining a vector comprising the individual capacities determined,
d) seeking a number of reference vectors having the shortest, in particular Euclidian, distance from the vector,
e) forming an interpolation function that, when applied to the reference vectors found in step b), provides the respective fill level associated with these reference vectors,
f) applying the interpolation function to the vector and using the result as the fill level.

Several preferred embodiments of the invention are described in greater detail by reference to the following drawings.

BRIEF DESCRIPTION OF THE SEVERAL VIEWS OF THE DRAWING

FIGS. 9a-12d show additional embodiments of containers having diagonal electrodes.

DESCRIPTION OF THE INVENTION

Figure 1:
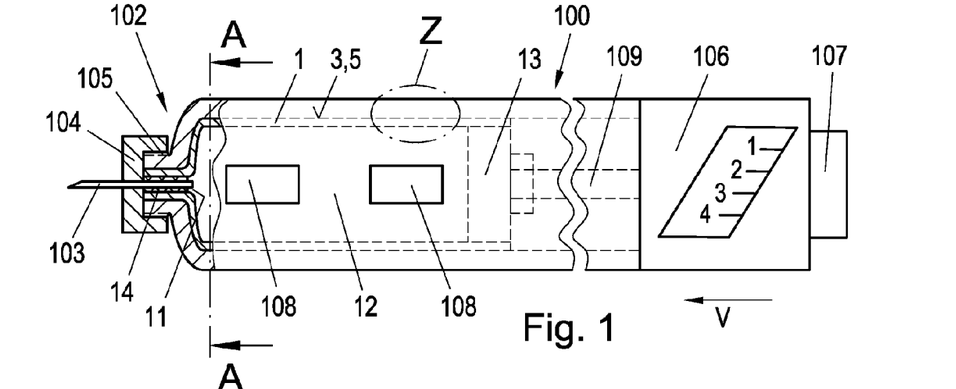
FIG. 1 shows a side view of a first embodiment of a dispensing device according to the invention.

FIG. 1 shows a side view of an embodiment of a dispensing device 100 according to the invention. The dispensing device 100 shown has a container 1 that is filled with a liquid drug 12. In this case, insulin is used as the liquid drug 12; however, it is also possible to use other liquid drugs 12, such as hormones (e.g., growth hormones, biopharmaceuticals, or drugs used in therapeutic measures in reproductive medicine) to be inserted into the container 1 and subsequently dispensed in this manner.

The dispensing device 100 is in the form of a pen, and may be comfortably held in the hand of a patient during the administration of the liquid 12 in the container 1. The container 1 is in the form of a cartridge or ampoule, and is in a terminal area 102 of the dispensing device 100.

Figure 2:
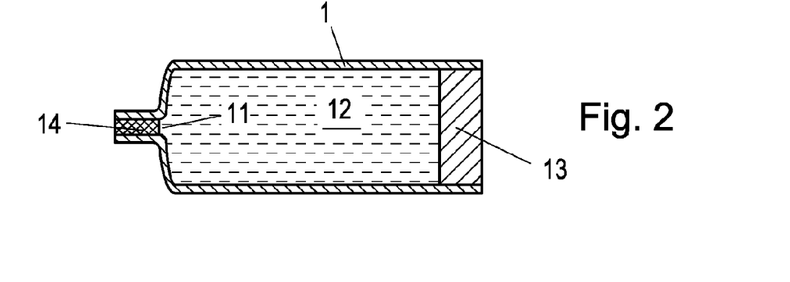
FIG. 2 shows a side view of a completely filled container in the form of an ampoule.

The container 1, which is shown in detail in FIG. 2, has an opening 11 for dispensing the liquid 12 on one end, which is in a terminal area 102 of the dispensing device 100. On the opposite end, the container 1 has a plunger 13 that is movably mounted inside the container 1. To this end, the container 1 has an internal volume with a constant cross section apart from the area of the opening 11. The plunger 13 seals the container 1 from the side opposite the opening 11, such that the liquid 12 in the container 1 is tightly sealed in the container 1 and can only exit through the opening 11. In this embodiment, the inside of the container 1 and the plunger 13 are circular in cross section and have a substantially cylindrical inner or outer wall. If the plunger 13 is pushed into the container, the liquid 12 in the container 1 can exit the container 1 through the opening 11. When the plunger 13 is pushed in the direction of the opening 11, the container 12 is dispensed from the container 1 through the opening 11. However, the opening 11 of the container 1, as shown in FIG. 2, is sealed by a seal 14 before use, such that the liquid 12 cannot exit the container 1.

Figure 3:
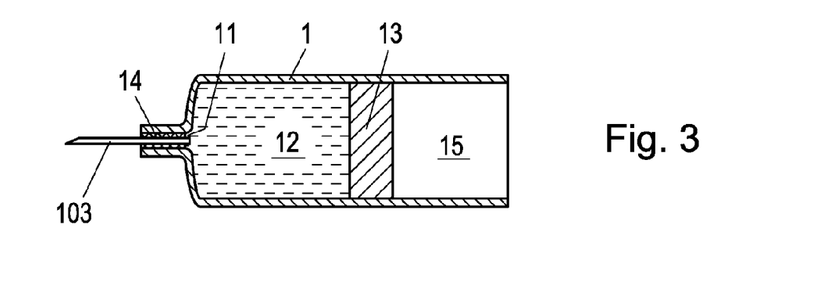
FIG. 3 shows a side view of a partially emptied container.

FIG. 3 shows the container 1 shown in FIG. 2 after some of the liquid 12 has been applied through the opening 11 via an injection needle 103.

Figure 4:
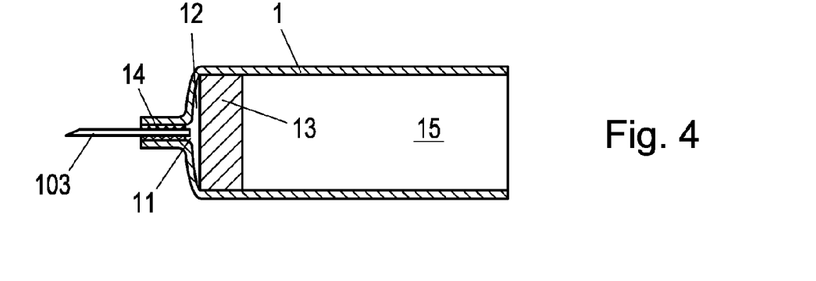
FIG. 4 shows a side view of a completely emptied container.

FIG. 4 shows the container 1 shown in FIG. 2 after the liquid 12 has been completely emptied from the container 1 through the opening 11 via an injection needle 103. As shown in FIGS. 3 and 4, the plunger 13 is in an intermediate or final position, i.e., the container 1 is partially (FIG. 3) or completely (FIG. 4) empty. There is air in the area 15 behind the plunger 13. The dispensing device 100 additionally has an injection needle 103 penetrating the seal 14 on the one hand and protruding into the container 1, and, on the other hand, protruding away from the dispensing device 1, in the area of the opening 11 of the container.

As shown in FIG. 1, the injection needle 103 in this exemplary embodiment is connected with a housing 104 that is screwed onto the dispensing device 100. The dispensing device 100 has outer threading 105 that is adapted to a corresponding inner threading of the housing 104. If the plunger 13 is pushed in the direction of the opening 11, as shown in FIG. 3, the liquid inside the container 1 can be administered through the opening 11 and the injection needle 103 to the respective patient. The housing of the dispensing device 100 has two view ports 108 in order to determine the fill level F of the liquid 12 remaining in the container 1 visually.

Additionally, the dispensing device 100 (FIG. 1) has a setting unit 106 with which a certain movement of the plunger 13 and—accordingly—a certain amount of the liquid 12 to be dispensed can be preset. After setting the amount of liquid 12 to be dispensed, a pressing element 109 is pressed against the plunger 13 of the container 1 by means of an actuator 107 pressed by the patient. The plunger 13 is pushed into the container 1, and the liquid 12 in the container 1 is administered to the patient via the injection needle 103. The pressing element 109 is secured against resetting against the direction of movement V of the plunger 13, i.e., away from the opening 11, such that the plunger 13 can only be moved further in the direction of the opening 11.

Figure 5:
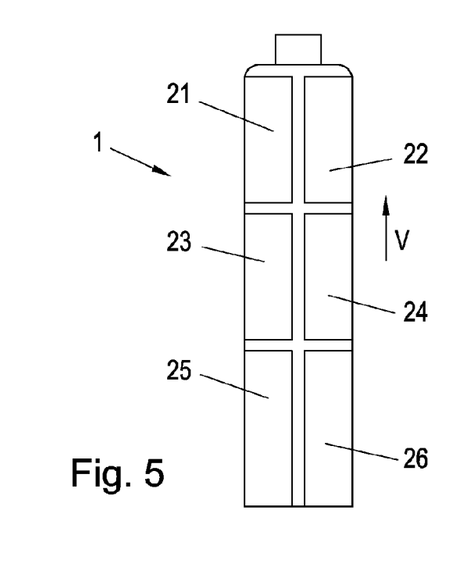
FIG. 5 shows an alternative embodiment of a container having three pairs of measurement electrodes.

It is particularly advantageous to use a container 1 with three pairs of measurement electrodes, as shown in FIG. 5. The container 1, as shown in FIG. 5, has three pairs of measurement electrodes 21-26. All measurement electrodes 21-26 are arranged on the outside of the container 1, in this case on the outer wall of the container 1. In this preferred exemplary embodiment of the invention, two associated measurement electrodes 21-26 each are opposite each other on the outer wall of the container 1, spaced apart in the circumferential direction. The individual pairs of associated measurement electrodes 21-26 are spaced apart in the direction of movement V of the plunger 13. The measurement electrodes 25, 26 of the third pair are farthest away from the opening 11 of the container 1. The measurement electrodes 21, 22 of the first pair are nearest to the opening 11. The measurement electrodes 23, 24 of the second electrode pair are—in the direction of movement V of the plunger 13—between the measurement electrodes 21, 22; 25, 26 of the first and third pair. The measurement electrodes 21-26 abut an area of the outer wall of the container 1 in a two-dimensional manner. In the exemplary embodiment shown in FIG. 5, the measurement electrodes 21-26 are rectangular in shape. The measurement electrodes 21-26 extend over the entire range of movement of the plunger 13. If multiple electrode pairs are used, it may be advantageous for the extension of one electrode pair in the direction of movement V of the plunger 13 to correspond to the extension of the plunger 13 in its direction of movement V.

Figure 6:
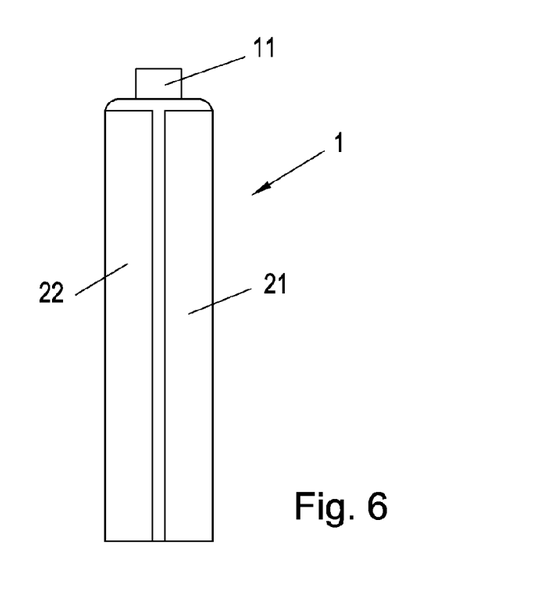
FIG. 6 shows a second embodiment of the invention having a single pair of measurement electrodes.

Alternatively, however, other electrode shapes, e.g., circular or comb-like electrode shapes may be used for the measurement electrodes 21-26. The use of several pairs of measurement electrodes 21-26 is generally advantageous for accurate measurement of the liquid content of level in elongated containers 1, but is not necessary in the case of short or compact containers 1. In an alternative exemplary embodiment of a container, shown in FIG. 6, only a single pair of measurement electrodes 21, 22 is provided that extend longitudinally over the entire range of movement. The two measurement electrodes 21, 22 are opposite one another circumferentially at the same height relative to the direction of movement V of the plunger 13.

Figure 7:
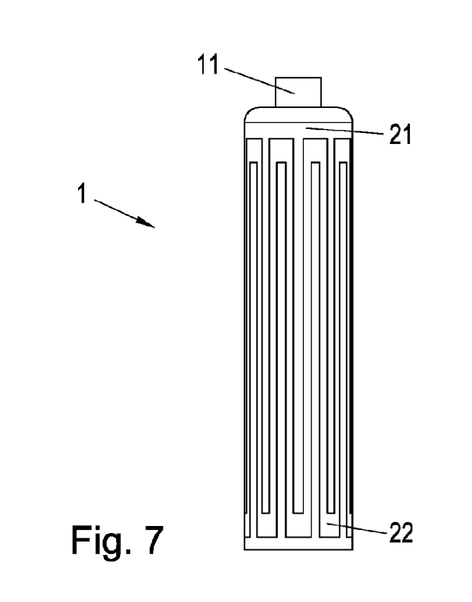
FIG. 7 shows another embodiment of the invention having a pair of measurement electrodes arranged in a comb configuration.
Figure 8:
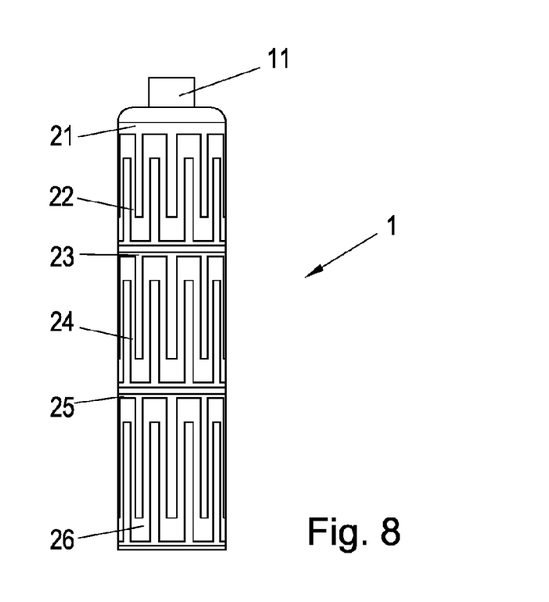
FIG. 8 shows another embodiment of the invention having threes pair of measurement electrodes arranged in a comb configuration.
Figure 9A:
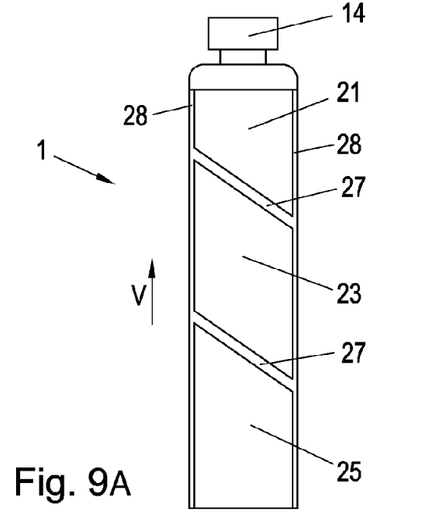
Figure 9B:
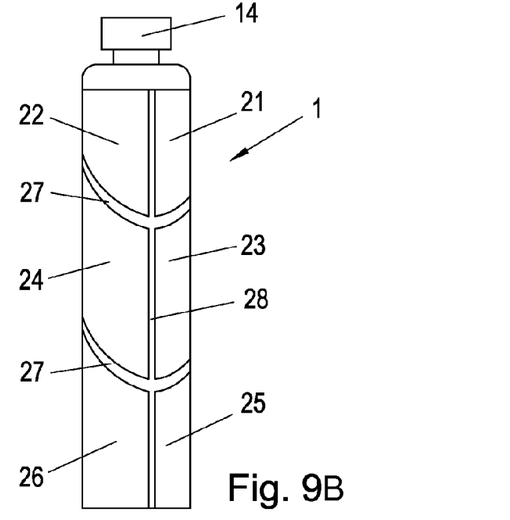
Figure 9C:
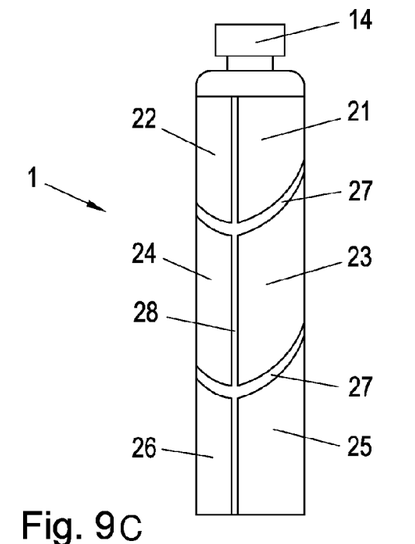
Figure 9D:
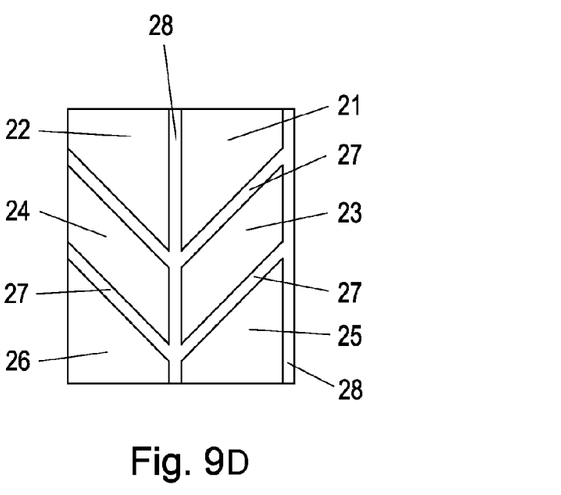
Figure 10A:
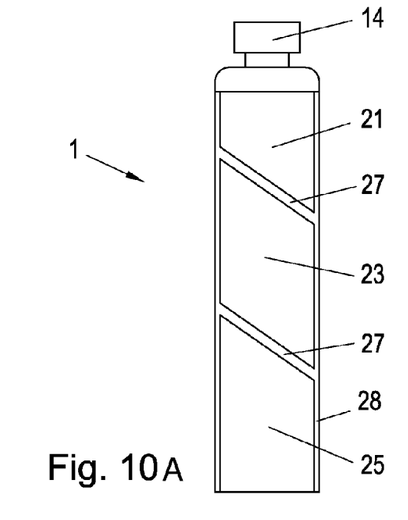
Figure 10B:
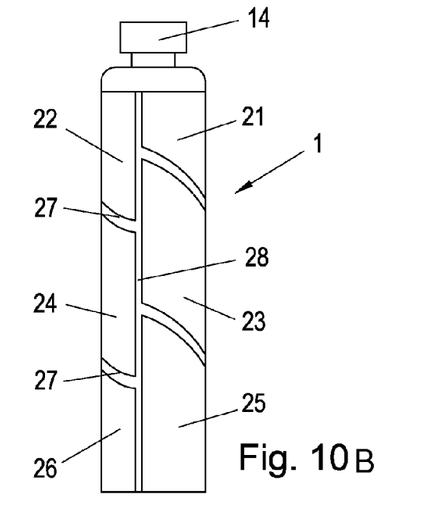
Figure 10C:
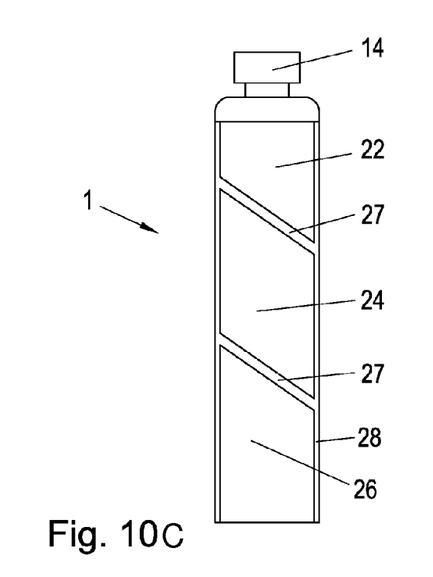
Figure 10D:
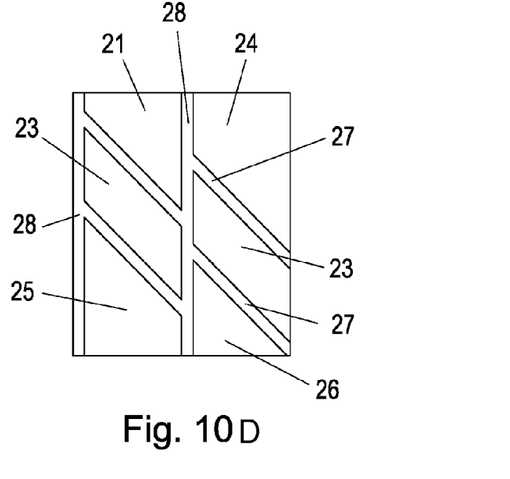
Figure 11A:
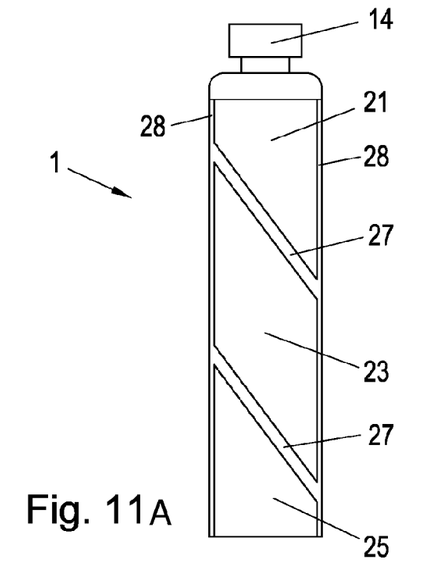
Figure 11B:
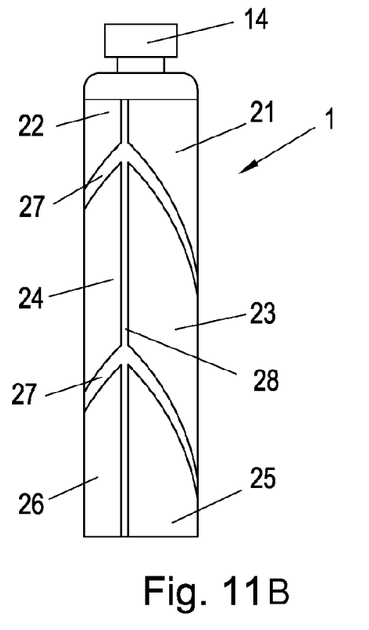
Figure 11C:
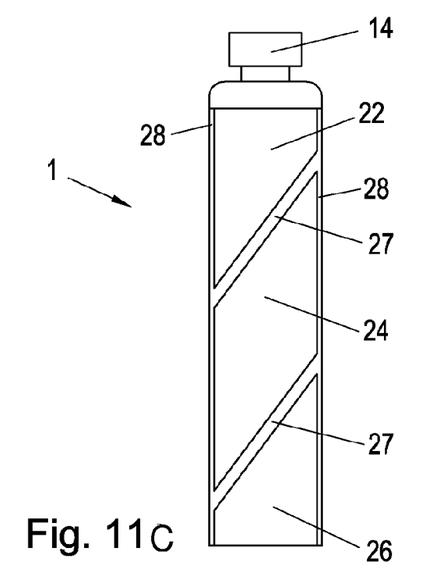
Figure 11D:
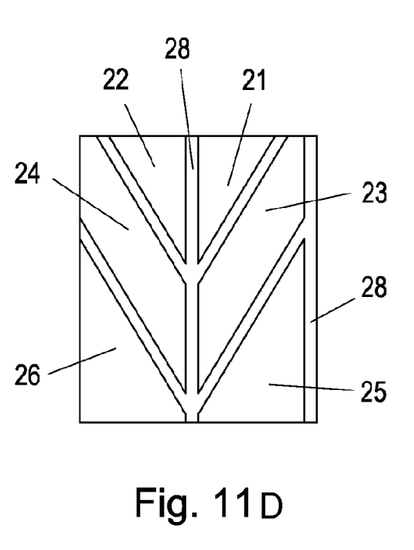
Figure 12A:
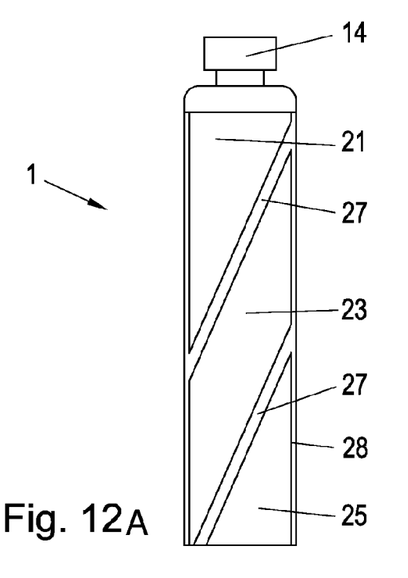
Figure 12B:
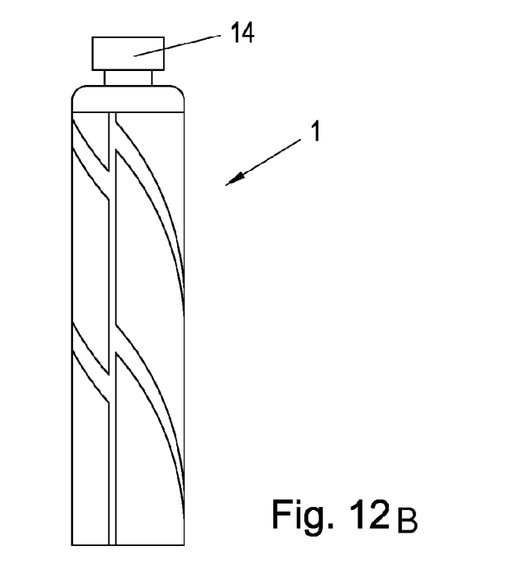
Figure 12C:
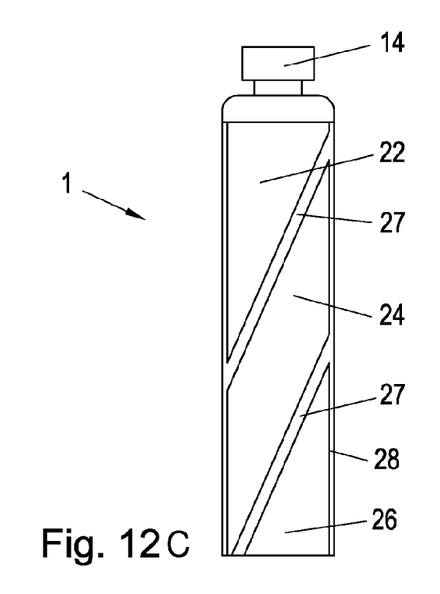
Figure 12D:
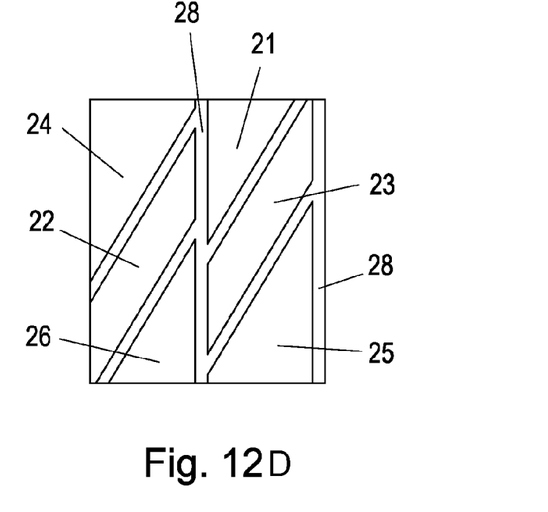

Additionally, it is also possible to use different shapes of measurement electrodes 21-26. An advantageous embodiment provides for the measurement electrodes 21-26 to be formed as comb electrodes or interdigital electrodes. The measurement electrodes 21-26 are paired and have a comb structure, whereby the teeth of associated measurement electrodes 21, 22; 23, 24; 25, 26 mutually engage. As shown in FIGS. 7 and 8, comb electrodes may be used both for an arrangement with one (FIG. 7) and with several pairs of measurement electrodes 21, 22; 23, 24; 25, 26.

Depending on the application, it is also possible to provide measurement electrodes 21-26 of different sizes in order to allow for particularly advantageous determination of the fill level F in the container 1. Particularly advantageous is the use of parallelogram-shaped or triangular measurement electrodes 21-26 in which the electrodes are separated by areas 27 of separation that run at an angle to the direction of movement V of the plunger or the longitudinal axis of the container 1, e.g., an angle of 45°. In such an arrangement, there is a fluid transition, such that particularly accurate determination of the fill level F is possible. FIGS. 9a-12d show four different embodiments with areas 27 between the measurement electrodes 21-26 at an angle to the direction of movement V. Additionally, in these embodiments, an axially parallel area 28 of separation is provided that separates respectively associated pairs of measurement electrodes 21, 22; 23, 24; 25, 26.

Figure 13:
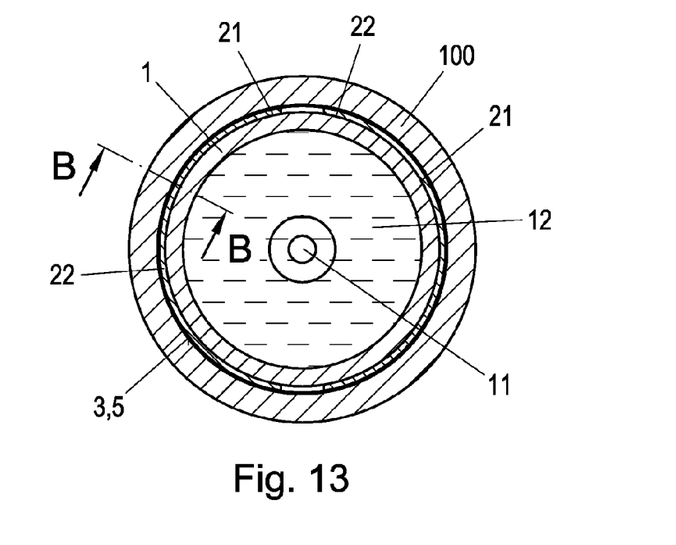
FIG. 13 shows a cross section of an embodiment of a device according to the invention.

With all such electrode arrangements, it is possible to deduce the fill level F of the container 1 from the capacity between the measurement electrodes 21-26. In order to allow for the most precise possible measurement of the individual capacities C1, C2, C3, thus allowing for a deduction of the fill level F of the container 1, the invention provides, in the setting of a dispensing device, for electrical insulation 3 for electrical fields outside of the measurement electrodes 21-26 to be arranged surrounding the container 1. FIG. 13 shows a section through the container 1 showing the cover 3, the measurement electrodes 21, 22, the wall of the container, and the liquid 12 inside the container 1. The cover 3 causes the capacity measured between the electrodes 21, 22 not to be falsified, or to be falsified to a negligible degree if a person touches or comes near to the dispensing device 100, thus changing the electrical field conditions present at the measurement electrodes 21, 22. In a first exemplary embodiment of the invention, the cover 3 is formed as a film of electrically conductive material, e.g., copper foil having a thickness of 50 µm, which is wrapped around the container 1 and the measurement electrodes 21, 22 abutting it so as to cover them. The measurement electrodes 21, 22 and the cover 3 are separate and not electrically connected with one another. The cover 3 serves to suppress the effect of external influences, e.g., changes in permittivity as well as electrical fields immediately outside the measurement electrodes 21, 22. The cover 3 surrounds both the measurement electrodes 21, 22 and the container 1, and is advantageously not between the measurement electrodes and the container 1.

Figure 13A:
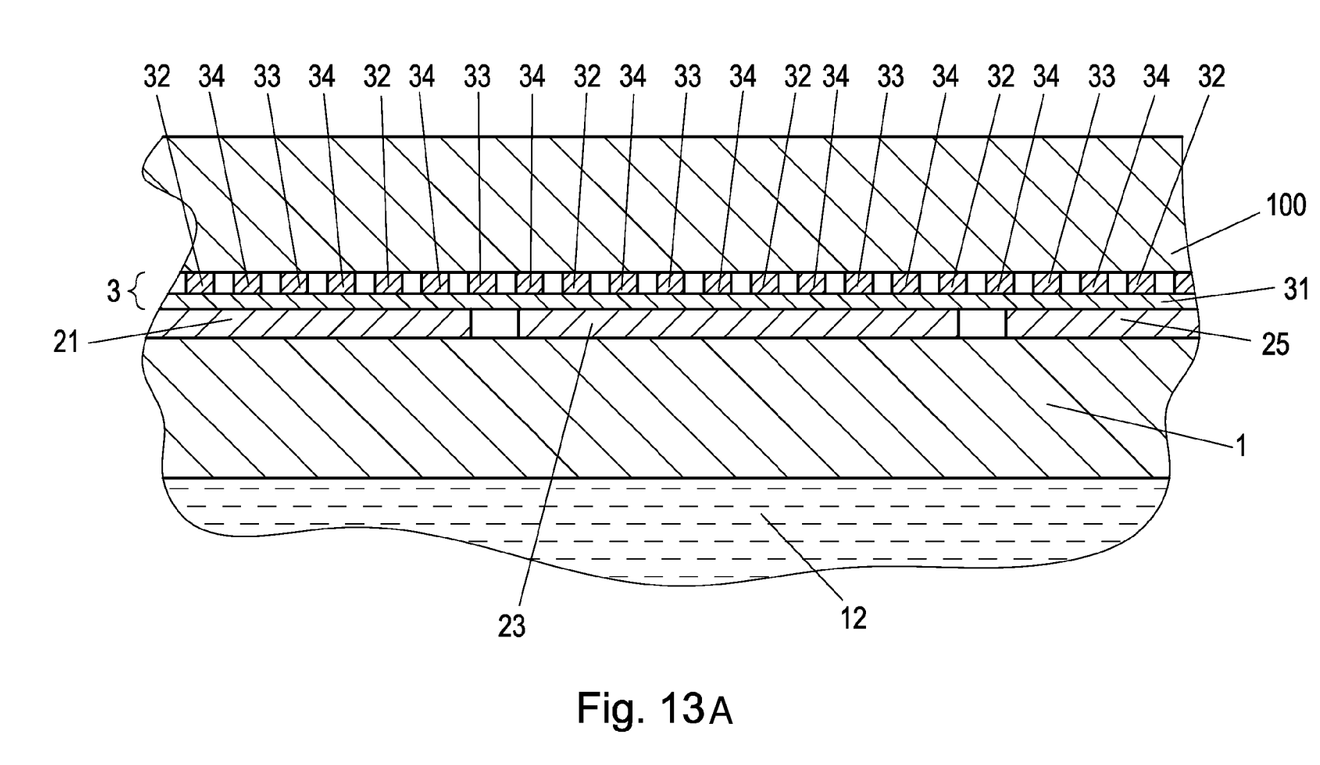
FIG. 13a shows a detail from FIG. 1.

FIG. 13a shows the detail Z of FIG. 1 in the section B-B of FIG. 13. The arrangement of the wall of the container 1 opposite the electrodes 21, 23, 25 and the cover 3 can clearly be seen, albeit not to scale. The individual conductors 32-34 on the film 3 are shown in section. The housing of the dispensing device 100 is outside the cover 3.

Alternatively, it is also possible to arrange the cover 3 immediately outside the outer wall of the dispensing device 100 and/or outside of a support at least partially enclosing the container 1.

Figure 14:
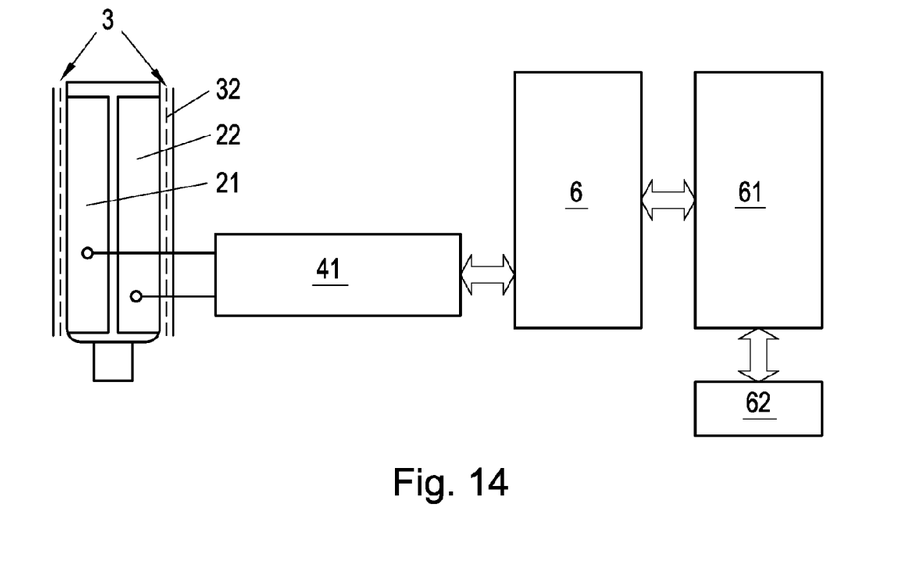
FIGS. 14 and 15 show two devices for determining the fill level inside the container and for transmitting the fill level determined to an external data communications device.
Figure 15:
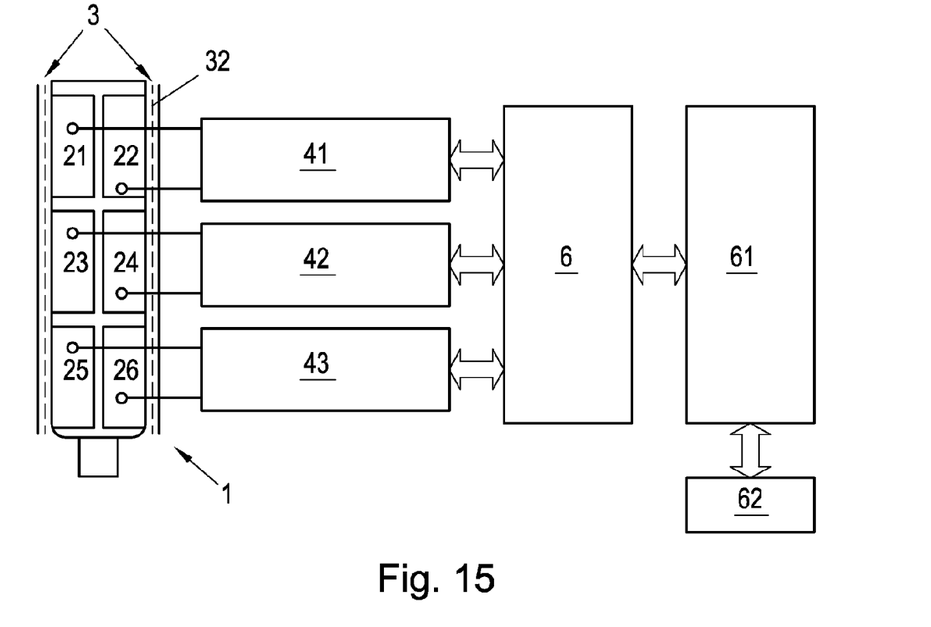

To determine the current fill level F of the liquid 12 in the container 1, first the existing capacity between the measurement electrodes 21, 22 is determined. FIG. 14 shows a measurement arrangement for determining the capacity of a single pair of measurement electrodes 21, 22. FIG. 15 shows a measurement arrangement in which several pairs of measurement electrodes 21-26 are used. In FIGS. 14 and 15, one processing unit 6 each is provided in the form of a microcontroller, upstream of which one or three capacity measurement systems 41, 42, 43 are arranged. Each pair of measurement electrodes 21-26 is associated with one of the capacity measurement devices 41, 42, 43 shown in FIG. 15. The measurement electrodes 21-26 are each connected with the connections of the capacity measurement devices 41, 42, 43. The output of each of the capacity measurement devices 41, 42, 43 is abutted by a capacity reading $C_1$, $C_2$, $C_3$ corresponding to the capacity of the respective electrode pair and representing it or proportional to it, which is transmitted to the processing unit 6. Based on the individual capacity readings $C_1$, $C_2$, $C_3$ transmitted, the processing unit 6 determines a value for the fill level F based on a calibration process described below. The processing unit 6 makes this value available at its output. This value may be transmitted, in particular, to an external data communications device (not shown) upon request via an antenna 62 downstream of the processing unit 6.

Of course, the number of pairs of measurement electrodes 21-26 used may be adapted to the accuracy requirements of the measurement. In particular, it is also possible to use a single pair of measurement electrodes 21, 22 and only to use the capacity reading $C_1$ obtained between these measurement electrodes 21, 22 to determine the fill level. (FIG. 15)

The processing unit 6 is upstream of a communication controller 61 that is connected to an antenna 62, in this case a spindle antenna. The communication controller 61 allows for the transmission of the fill level F determined to an external data communications device. It may also be provided for the external data communications device to transmit electrical energy via the antenna 62 to the communication controller 61, processing unit 6, and the capacity measurement devices 41-43 such that the entire circuit shown in FIGS. 14 and 15 can operate without a separate power supply.

Figure 17:
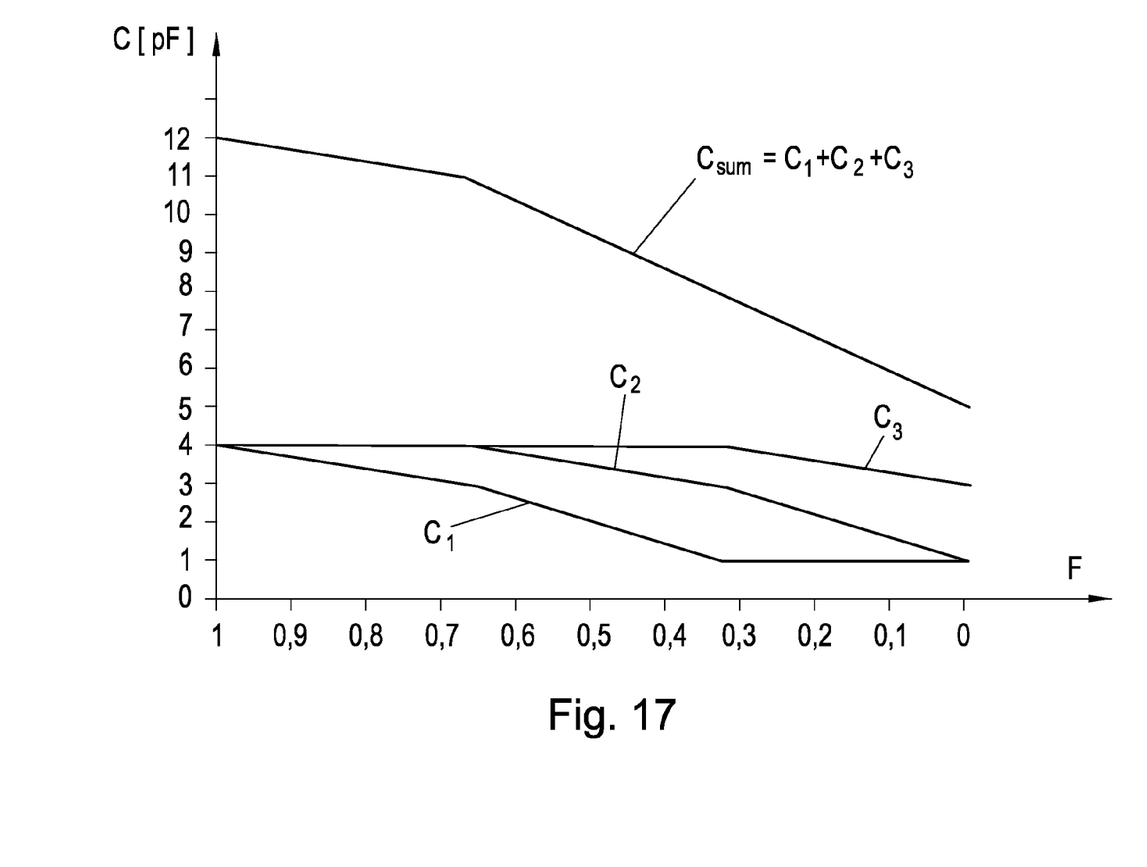
FIG. 17 shows the theoretical course of the individual partial capacities during the emptying of the container in the embodiment shown in FIG. 15.

In the following, the specific determination of the fill level F of the liquid 12 in the container 1 is shown in detail based on the capacity readings $C_1$, $C_2$, $C_3$ obtained. In FIG. 17, the dependency of the individual capacity readings $C_1$, $C_2$, $C_3$ on the fill level F in the embodiment of a container 1 according to the invention shown in FIG. 5 is shown schematically. At the beginning of the emptying of the container 1, only the liquid 12 is between the measurement electrodes 21-26. During emptying, the plunger 13 first enters the space between the measurement electrodes 21, 22 of the first measurement electrode pair such that, due to the lower permittivity of the plunger 13 relative to the liquid 12, continuous reduction of the capacity reading $C_1$ of the first measurement electrode pair can be seen. After the plunger 13 has been pushed through the area between the measurement electrodes 21, 22 of the first measurement electrode pair, there is air 15 between the two measurement electrodes 21, 22 of the first measurement electrode pair. Due to the even lower permittivity of the air between the two measurement electrodes 21, 22 of the first measurement electrode pair, the capacity reading $C_1$ obtained between these measurement electrodes 21, 22 decreases even further. Similar behaviour can also be seen for the capacity readings $C_2$, $C_3$ between the measurement electrodes 23-26 of the second and third measurement electrode pairs during the emptying of the container 1.

In a particular embodiment of the invention, the sum $C_{sum}$ of the individual capacity readings $C_1$, $C_2$, $C_3$ may be used to determine the fill level F. By determining a calibration curve, for a number of different fill levels, the related sum $C_{sum}$ of individual capacity readings $C_1$, $C_2$, $C_3$ may be determined, whereby each fill level F is associated with a sum $C_{sum}$. The data sets thus generated, each comprising a capacity reading $C_{sum}$ and a fill level F, are saved in a calibration memory in the processing unit 6.

After measuring and determining the individual capacity readings $C_1$, $C_2$, $C_3$, their sum $C_{sum}$ is determined and compared with the individual sums $C_{sum}$ saved in the calibration memory. The pair is selected, the sum $C_{sum}$ of which best matches the sum of the capacity readings $C_1$, $C_2$, $C_3$ obtained. The fill level associated with the best match $C_{sum}$ is considered the fill level F of the container 1; the processing unit 6 provides this fill level F at its output and, upon request, transmits this fill level F, as described above, to an external data communications device via an antenna 62.

Practice shows that—apparently due to complex capacitive coupling phenomena of the measurement electrodes 21-26, there are substantial deviations in the development of the measured capacities $C_1$, $C_2$, $C_3$ depending on the fill level F, which significantly deviate from the theoretically expected developments clearly shown in FIG. 17. The measurable curves, however, are easily reproduced and show different grades in different sections of curves or fill level ranges for each capacity $C_1$, $C_2$, $C_3$, whereby, contrary to theoretical expectations, the highest grade of a curve or the greatest change in capacity is not necessarily between the measurement electrodes 21-26 between which the fluid level is currently located. Because, however, higher grade means better measurement resolution/accuracy, for the calculation of the fill level, a weighted sum may be used as an alternative to the formation of a simple sum of the three individual capacity readings, whereby, for each of the three summands in each section of a curve, a separate weight is determined during calibration.

In order to convert between individual capacities $C_1, C_2, C_3$ and a fill level F, a calibration is carried out in which the container 1 filled with the drug or a reference container having the same structure is emptied. During emptying, the fill level F and the individual capacities $C_1, C_2, C_3$ are each determined. For each of the fill levels F reached during emptying, thus, individual capacity values $C_1, C_2, C_3$ are available. In this exemplary embodiment, 30 equidistant fill levels F are reached during emptying, whereby the initial state is designated 1 and the completely emptied state 0. The capacity readings $C_1, C_2, C_3$ are each saved in a reference vector $V_{ref}$ associated with the respective fill level F and the respective weights a, b, c. Thus, a reference vector $V_{ref}$ is available for each fill level F. The weights are determined by optimisation such that the weighted sum a. C1+b. $C_2$+C. $C_3$ is a linear approach to the fill level F.

In order to determine the actual fill level F based on the capacity readings $C_1, C_2, C_3$ determined by measurements, this can be done based on the weights obtained during calibration, whereby as many weights are available for each measurement as capacity readings $C_1, C_2, C_3$ were obtained. First, based on the capacity readings $C_1, C_2, C_3$ determined or measured, a vector $V_{mess}$-[$C_1, C_2, C_3$] is generated having the capacity readings $C_1, C_2, C_3$ as components. Then, the vector $V_{mess}$ is compared with the reference vectors determined and the reference vector at the shortest distance to the vector $V_{mess}$ is sought. In this exemplary embodiment, the Euclidian distance is used as the measure of distance. Then, the reference vectors $V_{ref}$ are determined that respectively have the next shortest distance from the vector $V_{mess}$. An interpolating function, e.g., a linear interpolation function, is determined that, when applied to the reference vectors $V_{ref}$ obtained by calibration, returns the respective associated fill level F. The capacity readings $C_1, C_2, C_3$ are used in the interpolation function, and an average fill level value.

The antenna 62 may advantageously be arranged on the outside of the cover 3 to save space. In order to provide an advantageous combination, the cover 3 has a film 31 consisting of an electrically and magnetically non-conductive material, e.g., plastic. Conductors 32-34 in the form of tracks are applied to the film 31, shown in FIG. 16. If the conductors 32-34 on the film 31 are formed such that there are no large closed conductor loops in which Foucault currents can form, the electromagnetic waves emitted by the external data communications device are not substantially affected by the cover 3 and may be received by the antenna 62. Additionally, this also makes it possible to transfer energy in the form of electromagnetic waves to the antenna 62 that is sufficient in order to supply adequate power to electrical components attached to the antenna.

To the extent that additional accuracy is required in determining the fill level F inside the container 1, it may be provided for a reading for the fill level F to be invalidated if the electrical field outside the container 1 is falsified, e.g., by contact or the approach of electrically conductive bodies or bodies with high dielectric permittivity.

Figure 16:
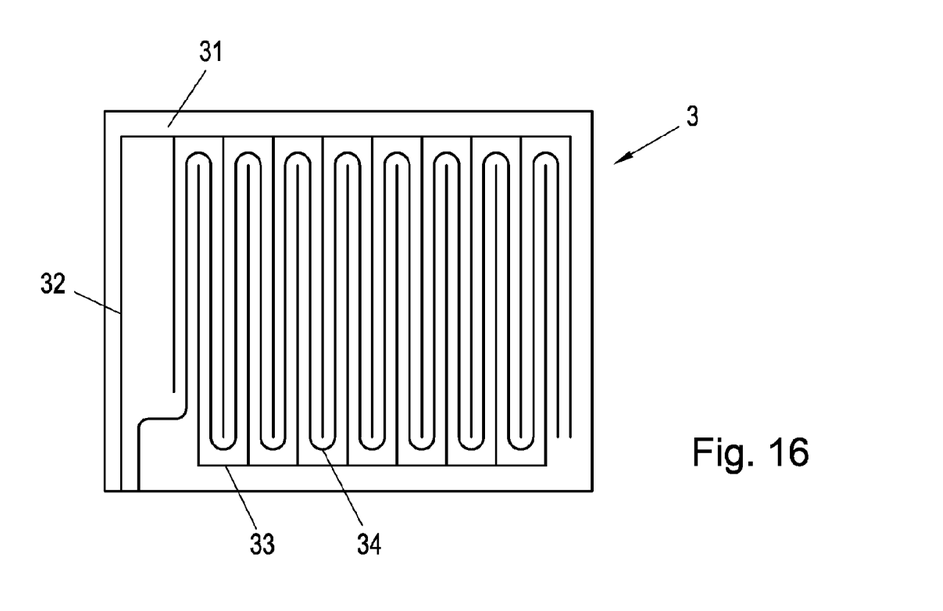
FIG. 16 shows a cover in the form of a film with conductors arranged thereon.

The cover 3 has an electrically and magnetically non-conductive film 31 on which multiple conductors 32, 33, 34 are formed by coating. The film 31 consists of flexible polymer in this exemplary embodiment. The tracks have a layer thickness of app. 50 μm and a width of approximately 1000 μm. Widths of the conductors 32-34 between 100 and 3000 μm are advantageous.

In order to avoid the formation of Foucault currents and resultant compromise of an NFC communication, the width of the conductors 32-34 may be limited to less than 3 mm. Additionally, the conductors 32-34, as shown in FIG. 16, may be formed free of loops, i.e., free of closed conductor loops, i.e., comprise no closed loops, in order to adequately prevent the formation of Foucault currents and avoid compromise of an NFC communication, whilst avoiding capacitive influences of the measurement electrodes 21-26 inside the cover 3.

In this particular exemplary embodiment of the invention, thus, two of the three conductors 32, 33 are formed as mutually engaging comb conductors 32, 33; the third conductor 34 runs between the two comb conductors 32, 33 in a meander configuration. In addition to this exemplary embodiment, of course, there are also numerous other exemplary embodiments of loop-free configuration of multiple tracks or electrodes on the surface of a film or inside or between individual layers of a multilayer film that are not electrically connected. The front and back of the film 31 may also be printed with conductors 32-34.

Alternatively, multiple meander-shaped conductors 34 may be arranged adjacent to one another between the comb conductors 32, 33, or several conductors 34 maybe arranged in a spiral on the film 31.

Figure 18:
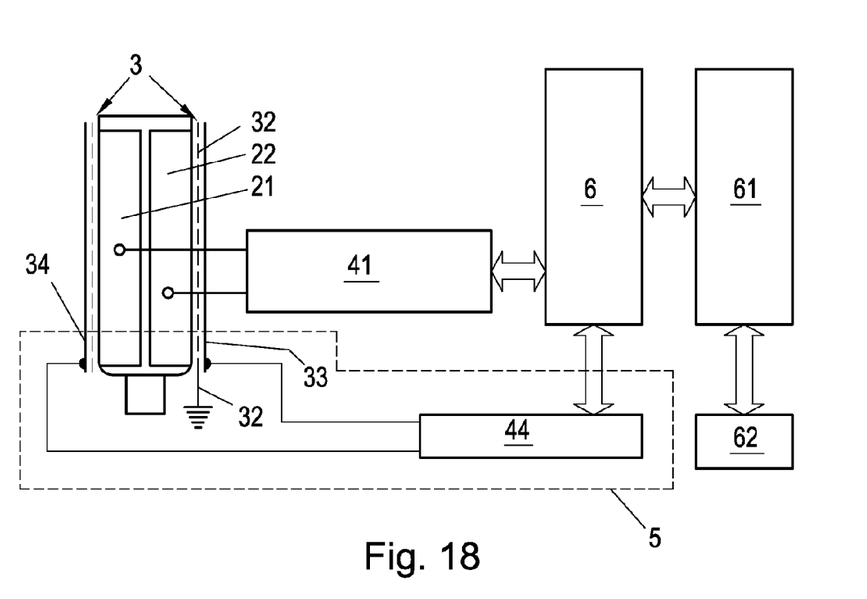
FIGS. 18 and 19 show the embodiments shown in FIGS. 14 and 15, whereby contact detection is additionally provided.
Figure 19:
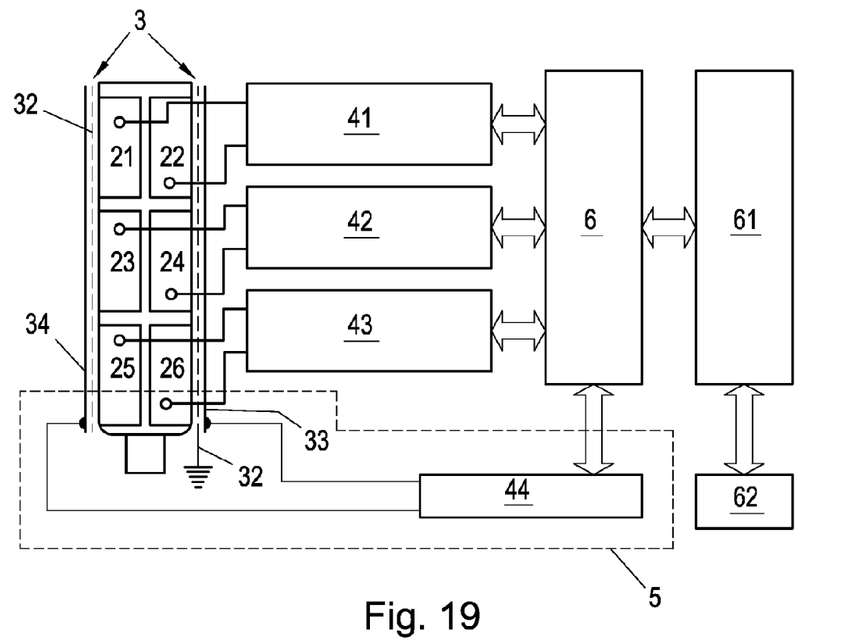

Two tracks, i.e., one of the two comb conductors 32 and the meander-shaped conductor 34, are used as a contact sensor 5. The second comb conductor 33 is set to a specified reference potential and serves as electrical insulation. If a person touches or approaches the cover 3, the change in permittivity of the environment changes the capacity between the conductors 32, 34 of the contact sensor 5. The change in this capacity between the conductors 32, 34 may be determined by means of another capacity measurement device 44; the conductors 32, 34 of the cover 3 or contact sensor 5 are connected to the measurement connections of the additional capacity measurement device 44. This additional capacity measurement device 44 determines an additional capacity reading C' and forwards it, as shown in FIGS. 18 and 19, to the processing unit 6.

If the change in the additional capacity reading C' obtained exceeds a specified threshold value T, it is assumed that the fill level F determined based on the capacity readings $C_1, C_2, C_3$ is erroneous due to the contact. The fill level F determined is invalidated.

In this particular exemplary embodiment, a cover 3 is used that simultaneously serves as a contact detector 5 and consists of the comb conductor 32 and the meander-shaped conductor 34. From a physical or functional standpoint, however, the electrical insulation 3 and contact detector 5 are two completely separate and distinct units that can be implemented particularly advantageously in the specific arrangement shown in FIG. 16, i.e., printed on one plane. This functional separation of electrical insulation 3 and contact detection 5 is, of course, simple to implement. The conductors 32, 33, 34 of the cover 3 or contact detection, which are on a single plane of the film 31, are shown adjacent to one another in FIGS. 14, 15, 18, and 19 merely for ease of illustration.

An alternative embodiment of the invention allows for the container 1 to be replaced in the dispensing device 100. A support (not shown) is arranged outside of the container 1 between the container 1 and the cover 3. Arranged thereon are measurement electrodes 21-26. The support abuts the container 1 and advantageously consists of part of the housing of the dispensing device 100. The measurement electrodes 21-26 are arranged on the wall of the support that abuts the container 1. The housing of the dispensing device 100 can be opened, and the container 1 can be removed from the housing of the dispensing device 100. The support is part of the dispensing device 100.

Advantageously, the communications controller, 61, the processing unit 6, the capacity measurement devices 41-44, and the antenna 62 may be arranged on the film 31.

The invention claimed is:

1. A device for dispensing liquids to persons, the device comprising:
    a container filled with a liquid having an opening formed therein on one end to dispense the liquid;
    at least one pair of capacitive measurement electrodes disposed on an outer side of said container opposite one another, to determine a permittivity of a respective medium in a space between said capacitive measurement electrodes;
    a cover surrounding said capacitive measurement electrodes and disposed around said container, said cover having a film coated with conductors in a form of tracks wrapped or disposed around said container, said conductors including first, second and third separate conductors formed on said film, said first and second conductors formed as mutually engaging comb conductors, said third conductor being meander-shaped and disposed between said two comb conductors;
    an area between the liquid and said capacitive measurement electrodes is free of said cover; and
    said cover is spaced apart from said capacitive measurement electrodes.

2. The device according to claim 1, wherein:
    said conductors are free of loops and free of closed conductor loops; and/or
    said conductors have a thickness of no more than 3 mm.

3. The device according to claim 1, further comprising:
    at least one unit selected from the group consisting of a communications controller, a number of capacitance measurement devices for determining a capacitance between said capacitive measurement electrodes, a processing unit, and an antenna to transmit readings determined by said capacitive measurement electrodes or to transmit fill level values derived from the readings, said at least one unit disposed on said film.

4. The device according to claim 1,
    further comprising a support disposed outside said container, between said container and said cover, said capacitive measurement electrodes disposed on said support and said support abuts said container; and/or
    wherein said capacitive measurement electrodes are disposed on a wall of said support abutting said container, whereby, said support forms a part of a housing of the device, or said support is connected with said housing.

5. The device according to claim 1, further comprising:
    a processing unit; and
    a communications controller with a downstream antenna connected to said processing unit, said antenna disposed on outside of said cover or directly on said cover, but not connected in an electrically conductive manner with said cover.

6. The device according to claim 1, further comprising:
    a processing unit; and
    a capacitance measuring device, said capacitive measurement electrodes disposed opposite one another are connected to said capacitance measuring device, and that a capacitance reading determined by said capacitance measurement device is supplied to said processing unit, said processing unit, based on the capacitance reading determined determines a fill level of the liquid in said container by means of a specified stored calibration function and makes the fill level determined available at an output.

7. The device according to claim 6, wherein:
    said capacitance measurement device has a reference connection; and
    one of said first, second and third conductors is connected to said reference connection of said capacitance measurement device.

8. The device according to claim 1,
    wherein said container has an internal volume having a constant internal cross section with an exception of an area of said opening; and
    a plunger sealing said container and the liquid contained in said container, said plunger having an outer cross section corresponding to a cross section of said internal volume of said container, and said plunger being disposed movably inside said container, such that, when said plunger is moved towards said opening, the liquid is dispensed out of said container through said opening.

9. The device according to claim 8, further comprising:
    a processing unit;
    a plurality of pairs of additional capacitive measurement electrodes disposed on said container, said pairs of additional capacitive measurement electrodes include said pair of capacitive measurement electrodes; and
    a plurality of additional capacitance measurement devices, one of said additional capacitance measurement devices is disposed downstream of each pair of said additional capacitive measurement electrodes for transferring a capacitance reading to said processing unit.

10. The device according to claim 9, wherein said additional capacitive measurement electrodes are opposite one another in a circumferential direction of said container, and, are at a same height in a direction of movement of said plunger.

11. The device according to claim 10, wherein:
    adjacent pairs of said additional capacitive measurement electrodes are disposed at a distance in a direction of movement of said plunger; and/or
    a width of said additional capacitive measurement electrodes corresponds to a width of said plunger in a direction of movement of said plunger.

12. The device according to claim 9, wherein:
    said additional capacitive measurement electrodes are disposed two-dimensionally on an outer surface of said container; and/or
    two of said pairs of said additional capacitive measurement electrodes are formed by two mutually engaging comb conductors that are disposed on an outer side of said container.

13. A device for dispensing liquids to persons, the device comprising:
    a container filled with a liquid having an opening formed therein on one end to dispense the liquid;
    at least one pair of capacitive measurement electrodes disposed on an outer side of said container opposite one another, to determine a permittivity of a respective medium in a space between said capacitive measurement electrodes;

a cover surrounding said capacitive measurement electrodes and disposed around said container, said cover having a first comb conductor and a meander-shaped conductor;

a contact sensor disposed outside or in an area of said cover, said contact sensor having said first comb conductor and said meander-shaped conductor of said cover as sensor electrodes;

a processing unit;

a capacitance measuring device; and said sensor electrodes of said contact sensor are connected to said capacitance measurement device, and an additional capacitance value determined by said capacitance measurement device is provided to said processing unit, and said processing unit suppresses a forwarding of a fill level determined by said processing unit or marks the fill level invalid if an additional capacitance reading exceeds a specified threshold value.

14. A method for determining and validating a fill level in a container disposed in a dispensing device, which comprises the steps of:

providing at least one pair of measurement electrodes disposed opposite one another on an outside of the container for measuring a capacitance;

determining the capacitance between the two measurement electrodes;

determining a fill level reading based on the capacitance determined according to a specified calibration function;

determining a further capacitance with conductors on the outside of the measurement electrodes in an area of a cover; and comparing the further capacitance with a threshold value, and the fill level is only considered valid if the further capacitance is below the threshold value.

15. The method according to claim 14, which further comprises transmitting at least one of the fill level or information on a validity of the fill level by encoded electromagnetic data transmission to an external data communications device.

16. The method according to claim 14, which further comprises:

determining capacitances of multiple pairs of measurement electrodes disposed opposite one another on the outside of the container; and determining the fill level based on the capacitances.

17. The method according to claim 16, which further comprises:

a) making available a respective reference vector containing the capacitances between the individual pairs of measurement electrodes as components for a number of fill levels;

b) associating a respective fill level with each of the reference vectors;

c) determining a vector containing the individual capacitances determined;

d) seeking a number of the reference vectors that are at a smallest distance, being a Euclidian distance, from the vector;

e) forming an interpolation function that, when applied to the reference vectors found in step b), provides the fill level associated with the reference vectors; and f) applying the interpolation function to the vector and a result is provided as the fill level.

* * * * *